US011419564B2

(12) United States Patent
Narabu

(10) Patent No.: US 11,419,564 B2
(45) Date of Patent: Aug. 23, 2022

(54) MEDICAL IMAGE DIAGNOSTIC APPARATUS, X-RAY DIAGNOSTIC APPARATUS, AND CONSOLE DEVICE FOR X-RAY DIAGNOSTIC APPARATUS

(71) Applicant: CANON MEDICAL SYSTEMS CORPORATION, Otawara (JP)

(72) Inventor: Yusuke Narabu, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 57 days.

(21) Appl. No.: 17/142,292

(22) Filed: Jan. 6, 2021

(65) Prior Publication Data

US 2021/0212645 A1    Jul. 15, 2021

(30) Foreign Application Priority Data

Jan. 10, 2020    (JP) .............................. JP2020-003234

(51) Int. Cl.
| A61B 6/00 | (2006.01) |
| G06F 3/02 | (2006.01) |
| G06F 3/14 | (2006.01) |
| A61B 8/00 | (2006.01) |

(52) U.S. Cl.
CPC ............ *A61B 6/467* (2013.01); *G06F 3/0202* (2013.01); *G06F 3/0227* (2013.01); *G06F 3/14* (2013.01); *A61B 8/467* (2013.01)

(58) Field of Classification Search
CPC ....... A61B 6/467; A61B 8/467; A61B 1/0052; A61B 34/74; A61B 1/00066; A61B 1/05; G06F 3/0227; G06F 3/0202; G06F 3/14
See application file for complete search history.

(56) References Cited

U.S. PATENT DOCUMENTS

| 6,349,616 B1 | 2/2002 | Onodera et al. |
| 2016/0220218 A1 | 8/2016 | Zaiki et al. |
| 2016/0247644 A1 | 8/2016 | Ishigure et al. |
| 2019/0290102 A1* | 9/2019 | Sasaki ................ A61B 1/00066 |

FOREIGN PATENT DOCUMENTS

| JP | 2000-142422 A | 5/2000 |
| JP | 2005-131000 A | 5/2005 |
| JP | 2016-140668 A | 8/2016 |
| JP | 2016-157615 A | 9/2016 |

* cited by examiner

*Primary Examiner* — Don K Wong
(74) *Attorney, Agent, or Firm* — Oblon, McClelland, Maier & Neustadt, L.L.P.

(57) ABSTRACT

According to an embodiment, a medical image diagnostic apparatus includes a switch and processing circuitry. The switch includes a detachable grip portion. The processing circuitry is configured to assign a function to the switch based on a type of the grip portion.

20 Claims, 12 Drawing Sheets

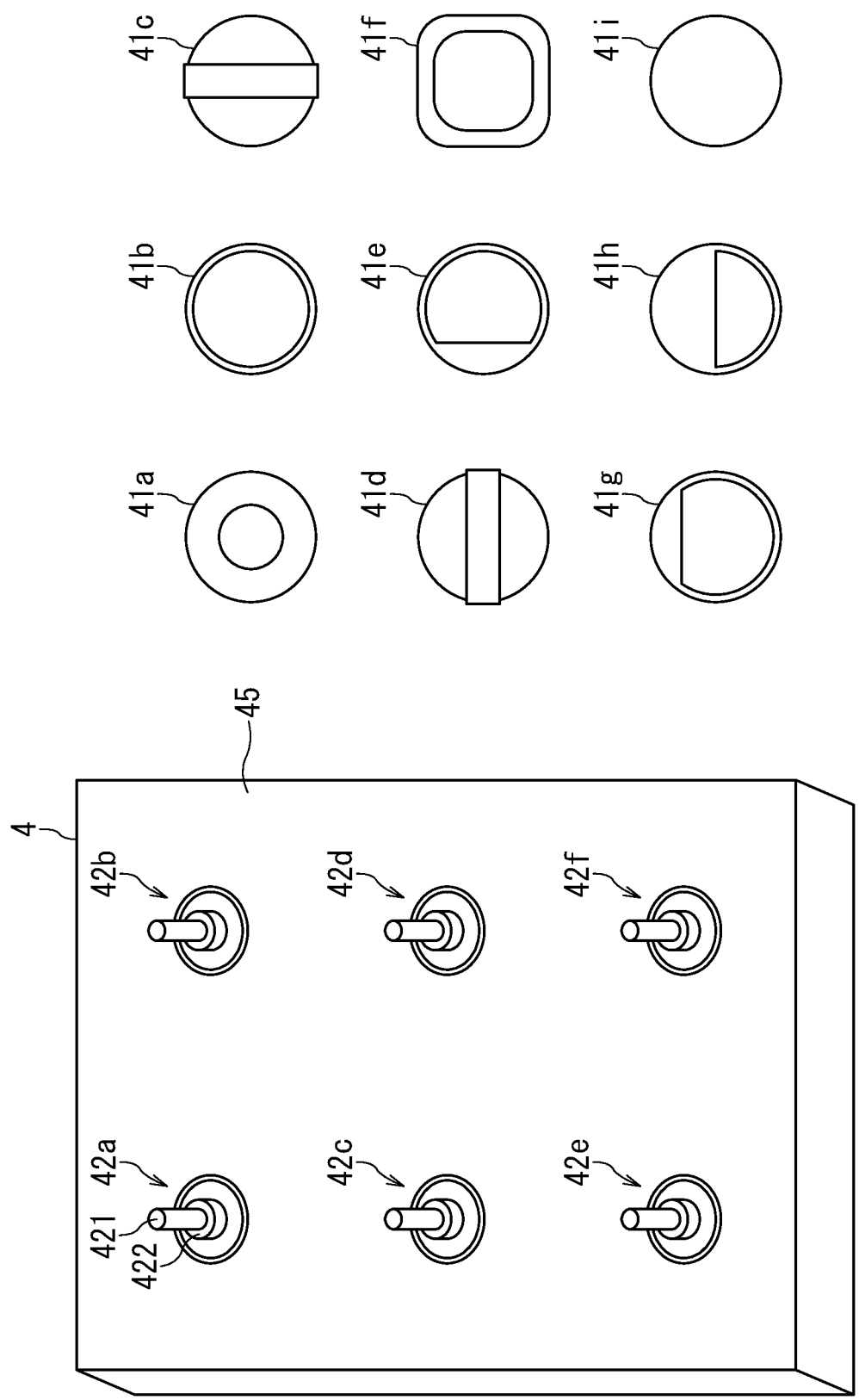

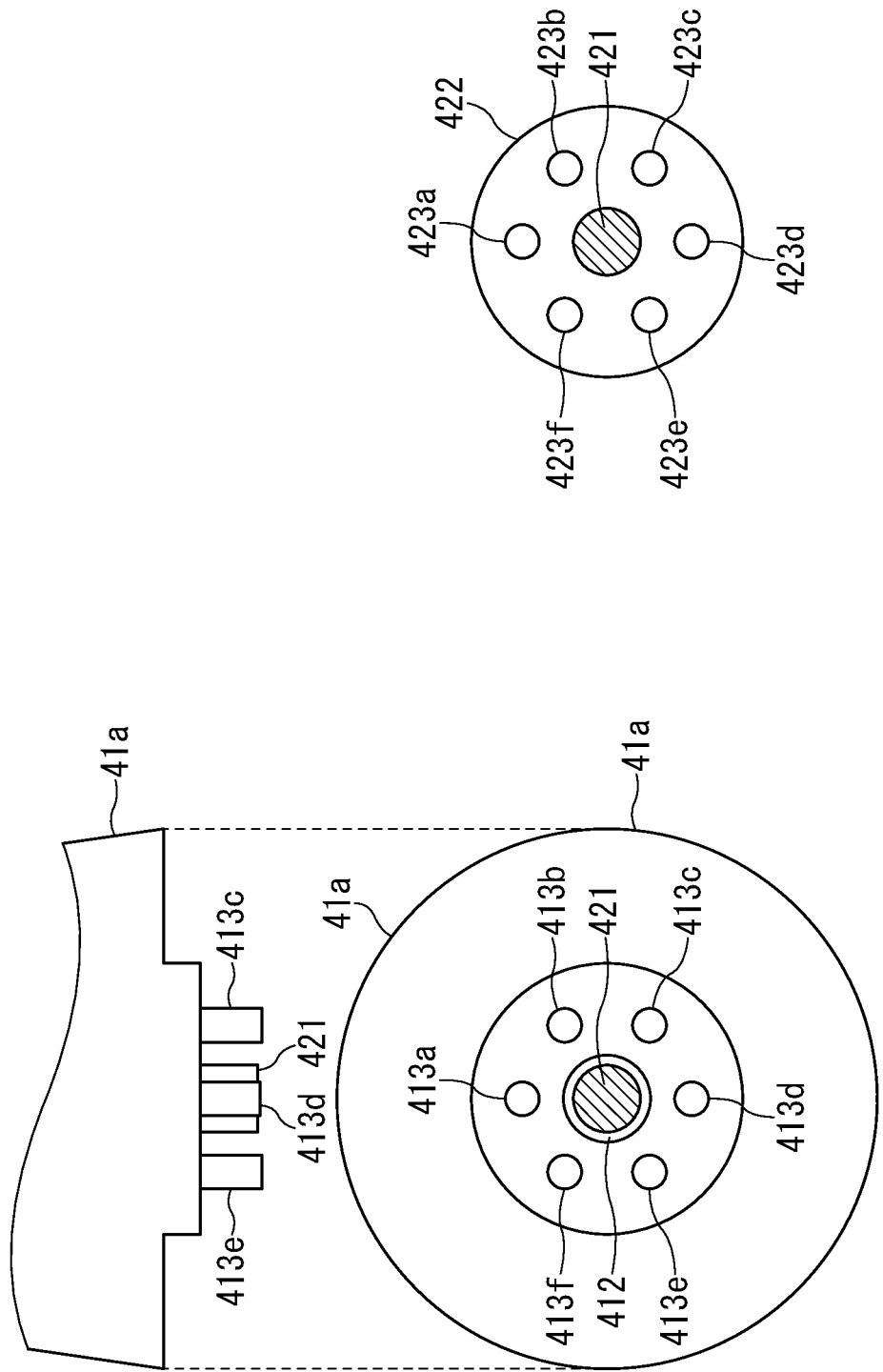

| | FIRST DETECTION PORTION | SECOND DETECTION PORTION | THIRD DETECTION PORTION | FOURTH DETECTION PORTION | FIFTH DETECTION PORTION | SIXTH DETECTION PORTION |
|---|---|---|---|---|---|---|
| FUNCTION 1 | ON | ON | ON | ON | ON | ON |
| FUNCTION 2 | ON | ON | ON | ON | ON | OFF |
| FUNCTION 3 | ON | ON | ON | ON | OFF | OFF |
| ... | ... | ... | ... | ... | ... | ... |
| FUNCTION 64 | OFF | OFF | OFF | OFF | OFF | OFF |

FIG. 7

| SWITCH POSITION | ASSIGNED FUNCTION |
|---|---|
| POSITION 1 | FUNCTION 1 |
| POSITION 2 | FUNCTION 10 |
| POSITION 3 | FUNCTION 15 |
| POSITION 4 | FUNCTION 20 |
| POSITION 5 | FUNCTION 25 |
| POSITION 6 | FUNCTION 30 |

FIG. 8

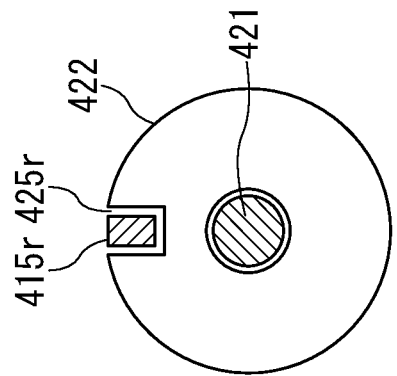
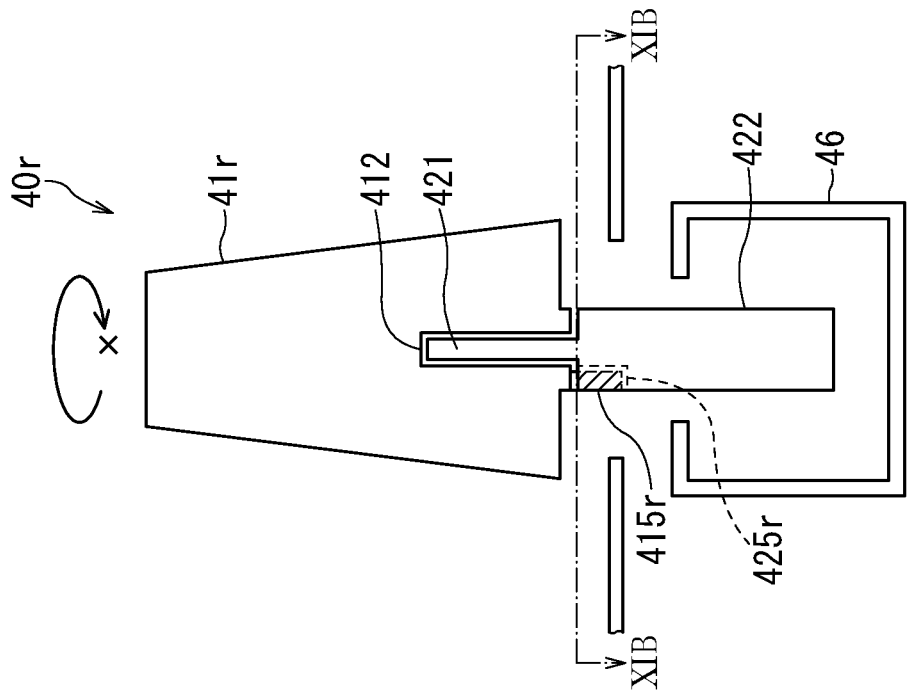
FIG. 11A
FIG. 11B

MEDICAL IMAGE DIAGNOSTIC APPARATUS, X-RAY DIAGNOSTIC APPARATUS, AND CONSOLE DEVICE FOR X-RAY DIAGNOSTIC APPARATUS

CROSS-REFERENCE TO RELATED APPLICATIONS

This application claims the benefit of priority of Japanese Patent Application No. 2020-003234, filed Jan. 10, 2020, the entire contents of which are incorporated herein by reference.

FIELD

Embodiments described herein relate generally to a medical image diagnostic apparatus, an X-ray diagnostic apparatus, and a console device for an X-ray diagnostic apparatus.

BACKGROUND

The X-ray diagnostic apparatus is known that can adjust the imaging part and imaging angle by attaching an X-ray generator and an X-ray detector to, for example, both ends of a C-arm, and moving or rotating the C-arm around the object. A biplane X-ray diagnostic apparatus provided with a ceiling-traveling Ω arm in addition to the C arm is also known. With the biplane X-ray diagnostic apparatus, a three-dimensional X-ray image of the object is collected by rotating the C arm and the Ω arm around the object.

Such X-ray diagnostic devices are provided with a bed device on which the object is placed. The object is placed on the tabletop of the bed device, and the position of the object at the time of imaging is adjusted by moving the tabletop in the vertical direction or the horizontal direction. Further, the X-ray diaphragm provided in the X-ray generator adjusts the X-ray irradiation amount and the X-ray irradiation range to the object. Still further, the size and position of the X-ray detector provided in the X-ray detector are changed according to the X-ray irradiation range.

These operations of the X-ray diagnostic apparatus are executed by the operation of the user. In general, users of the medical image diagnostic apparatus such as the X-ray diagnostic apparatus and the ultrasonic diagnostic apparatus operates components of the medical image diagnostic apparatus through an input means such as a switch that is provided on the medical image diagnostic apparatus and/or a console device of the medical image diagnostic apparatus. Therefore, the input means is generally provided with a plurality of switches for performing different functions.

The arrangement of switches and the functions assigned to switches are normally determined at the time of product shipment or installation. Meanwhile, the optimal arrangement of the switches depends on the user. However, the arrangement and type of the plurality of switches provided in such input means cannot be easily changed according to the request of the user.

BRIEF DESCRIPTION OF THE DRAWINGS

FIG. 2A is a perspective view showing an example of a console device without a switch cap.

FIG. 2B is an explanatory view showing an example of a plurality of switch caps having different shapes.

FIG. 4A is a sectional view taken along line IVA-IVA of FIG. 3B showing an example of the recognition function provided on the switch of the console device.

FIG. 4B is a sectional view taken along line IVB-IVB of FIG. 3B.

FIG. 7 is a table showing an example of a combination table of the X-ray diagnostic apparatus according to the first embodiment.

FIG. 8 is a table showing an example of a switch table of the X-ray diagnostic apparatus according to the first embodiment.

FIG. 11A is a sectional view showing an example of the rotation suppression mechanism of the switch of the X-ray diagnostic apparatus according to the third embodiment.

FIG. 11B is a sectional view taken along line XIB-XIB of FIG. 11A.

DETAILED DESCRIPTION

Hereinbelow, a description will be given of a medical image diagnostic apparatus, an X-ray diagnostic apparatus, and a console device for an X-ray diagnostic apparatus according to embodiments with reference to the drawings.

A medical image diagnostic apparatus according to an embodiment includes a switch and processing circuitry. The switch includes a detachable grip portion. The processing circuitry is configured to assign a function to the switch based on a type of the grip portion.

The medical image diagnostic apparatus according to the embodiments is a medical image diagnostic apparatus that receives an instruction of a user via an input means having a switch, and for example, an ultrasonic diagnostic apparatus or an X-ray diagnostic apparatus can be used as the medical image diagnostic apparatus. In the following description, an example of using an X-ray diagnostic apparatus as the medical image diagnostic apparatus according to the embodiments will be shown.

Overall Structure

Figure 1:
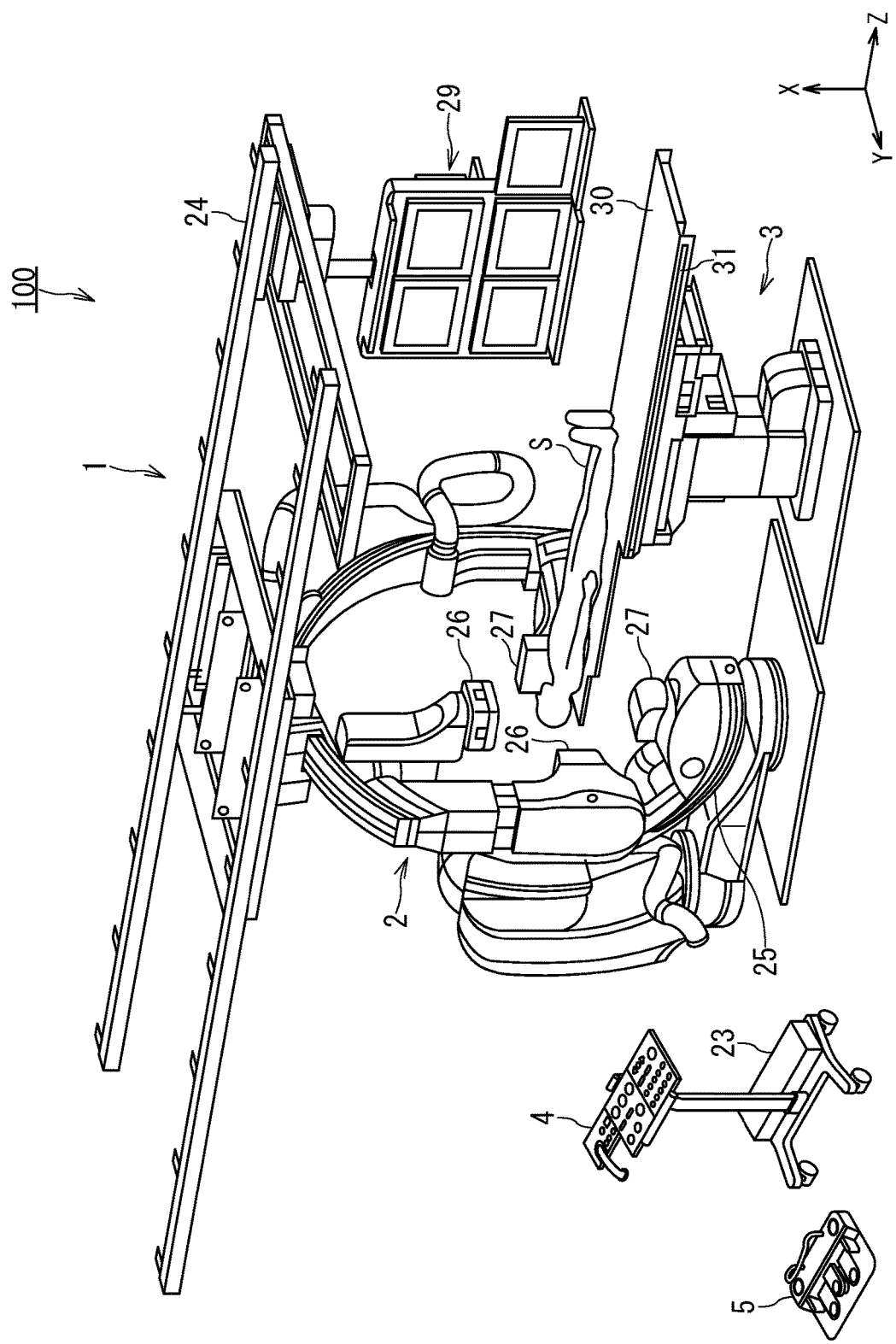
FIG. 1 is a schematic configuration diagram showing an example of an X-ray diagnostic apparatus according to an embodiment.

FIG. 1 is a schematic configuration diagram showing an example of an X-ray diagnostic apparatus 100 according to an embodiment.

The X-ray diagnostic apparatus 100 as an example of the medical image diagnostic apparatus includes an imaging device 2, a bed device 3, a console device 4, and a foot switch 5.

The imaging device 2 is, for example, a biplane X-ray imaging apparatus having a C arm and an Ω arm. The C-arm is fixed to the floor or wall of the imaging room. The Ω arm is configured to be able to travel on the ceiling. In the example of FIG. 1, a biplane X-ray imaging apparatus is shown, but the imaging system may be a single plane X-ray imaging device.

As shown in FIG. 1, each of the C arm and the Ω arm of the imaging device 2 has an X-ray generator 26 and an X-ray detector 27. The X-ray generator 26 and the X-ray detector 27 are arranged at both ends of each arm so as to face each other.

The X-ray generator 26 and the X-ray detector 27 arranged at both ends of the C-arm can be rotated around the object S around two axes, a chord of the C-arm and an axis perpendicular to the chord, by a C-arm drive device (not shown).

Similarly, the X-ray generator 26 and the X-ray detector 27 arranged at both ends of the Ω arm can be rotated around object S by two axes, the chord of the Ω arm and the axis perpendicular to the chord, by the Ω arm drive device (not shown).

Further, the X-ray detector 27 of the C arm and the Ω arm can be moved in parallel with the chords of the arm.

The Ω arm includes a transportation means such as wheels. The Ω arm moves horizontally along, for example, a rail 24 laid on the ceiling of the examination room. In the example of FIG. 1, an example in which the rail 24 is laid on the ceiling is shown, but the rail 24 may be laid on the floor, and the Ω arm may move horizontally along the rail laid on the floor. Further, the Ω arm may be expanded and contracted in the vertical direction.

The X-ray generator 26 has an X-ray tube and a diaphragm device. The X-ray tube is provided with high-voltage power by a high-voltage power source and generates X-rays according to the conditions of high-voltage power.

The diaphragm device narrows down the X-ray irradiation range such that the imaging region of object S is selectively irradiated with X-rays by, for example, sliding a plurality of diaphragm blades. Further, the diaphragm device adjusts the amount of X-ray irradiation to the object S by adjusting the opening degree of the diaphragm blades.

The X-ray detector 27 includes a flat panel detector (FPD), an FPD adjuster, and an A/D (analog to digital) converter. The FPD has a plurality of detection elements arranged in two dimensions. The FPD adjuster may change the detection area of the FPD and rotates the FPD. Further, the FPD adjuster may change from a normal sensitivity FPD to a high-definition FPD having high sensitivity detection elements. The A/D converter converts the time-series analog signal output from the FPD into a digital signal and transmits it to the control device of the X-ray diagnostic apparatus 100. The control device of the X-ray diagnostic apparatus 100 generates an X-ray image from the received digital signal.

The control device of the X-ray diagnostic apparatus 100 is provided, for example, in a machine room separate from the examination room. The control device has control circuits such as processing circuitry, memory, and image processing circuitry, and controls the entire X-ray diagnostic apparatus 100. Each of these control circuits includes a processor, and the processor executes a program stored in memory to realize various functions. For example, the processor of the image processing circuit executes an image processing program stored in memory, generates the X-ray image, and displays it on display 29.

The memory is equipped with a configuration including a storage medium that can be read by a processor, such as a magnetic memory medium, an optical memory medium, and a semiconductor memory. The memory may be configured such that some or all of the program and data in those storage media can be downloaded by means of communication via an electronic network, or can be given via a portable storage medium such as an optical disk. A part or all of the information stored in the memory may be distributed and stored or duplicated in at least one of a storage medium such as an external memory or another memory possessed by the X-ray diagnostic apparatus 100 (not shown).

The display 29 is configured by a general display device such as a liquid crystal display or an OLED (Organic Light Emitting Diode) display, and displays the X-ray image under the control of the control circuits.

The bed device 3 has a tabletop 30, an accessory attachment rail 31, a support base, and a tabletop drive device arranged in the support base. Object S is placed on the tabletop 30.

The support base movably supports the tabletop 30 in the horizontal direction (Z-axis direction of the device coordinate system). The tabletop drive device moves the tabletop 30 in the Z-axis direction of the device coordinate system. Further, the tabletop drive device moves the tabletop 30 in parallel with the X-axis direction to raise and lower the tabletop 30.

Hereinafter, in the present specification, unless otherwise specified, the X-axis, Y-axis, and Z-axis of the above-mentioned device coordinate system are defined as follows. First, the vertical direction is defined as the X-axis, and the tabletop 30 is arranged so that the normal direction of the upper surface thereof is the X-axis direction. The horizontal movement direction of the tabletop 30 is defined as the Z axis, and the tabletop 30 is arranged so that its longitudinal direction is the Z axis direction. The Y-axis is orthogonal to the X-axis and the Z-axis.

The console device 4 is a console device 4 designed for the X-ray diagnostic apparatus. The console device 4 is fixed to the stand 23. The console device 4 is a switch panel in which a plurality of switches are arranged (hereinafter, simply referred to as a console device 4) that accepts operations for executing a plurality of functions realized by components of the X-ray diagnostic apparatus 100. A plurality of switches provided in the console device 4 output an operation input signal corresponding to the operation on the switch to the processing circuitry.

Here, the switch is an input device that accepts operations from the outside. The switch can not only output a signal corresponding to on/off switching, but also output an operation input signal according to a force (operation amount) received from the outside. For example, in the case of a lever-shaped switch, an operation input signal corresponding to the operation direction of the lever and the inclination angle of the lever is output to processing circuitry as a continuous quantity.

The X-ray diagnostic apparatus 100 further includes an input circuit realized by general input devices such as a trackball, a mouse, a keyboard, a touch pad that performs an input operation by touching an operation surface, a contactless input circuit using an optical sensor, a voice input circuit, and the like. The input circuit outputs an operation input signal corresponding to the operation of the user to the processing circuitry.

In the following description, each component of the X-ray diagnostic apparatus 100 including the imaging device 2 and the bed device 3 is collectively referred to as the "operation target device 1". The console device 4 is a controller that operates the operation target device 1.

The foot switch 5 is provided with a plurality of foot-operated switches. The foot switch 5 also has a plurality of switches, like the console device 4, that accept operations for executing a plurality of functions of the operation target device 1.

As described above, the X-ray diagnostic apparatus 100 has a plurality of devices such as imaging device 2 and bed device 3. Each of these devices has multiple functions. As described above, the functions of the X-ray diagnostic apparatus 100 are diverse. A plurality of functions included in the X-ray diagnostic apparatus 100 are assigned to each switch provided on the console device 4, the foot switch 5, the imaging device 2, and the bed device 3. The user selects a switch corresponding to a desired function from the switches provided in the X-ray diagnostic apparatus 100 and the console device 4. The function desired by the user is executed by operating the selected switch.

First Embodiment

The arrangement and type of switches provided on the X-ray diagnostic apparatus 100 and the console device 4 are predetermined at the time of product shipment or installation. Therefore, conventionally, it has not been easy to arrange the switches freely or change the switches to the switches corresponding to the desired operation.

Hence, in order to solve the above problems, the X-ray diagnostic apparatus 100 and the console device 4 for the X-ray diagnostic apparatus according to the first embodiment have a recognition function that recognizes a function associated with the grip portion of the switch and assigns the recognized function to the switch to which the grip portion is attached. The grip portion is, for example, a switch cap attached to the operation portion of the switch.

(1) Configuration

FIGS. 2A and 2B are schematic views showing an example of the console device 4 for the X-ray diagnostic apparatus according to the first embodiment. FIG. 2A is a schematic view of the console device 4 in a state where the switch cap 41 is not attached. FIG. 2B is a schematic view of a plurality of switch caps 41 having different shapes.

The console device 4 illustrated in FIG. 2A is provided with six switch shafts 42a to 42f corresponding to the six switches, respectively. In the following description, the state in which the switch cap 41 is attached to the switch shaft 42 provided on the console device 4 or the X-ray diagnostic apparatus 100 is referred to as a "switch". Further, the position where the switch shaft 42 is arranged is referred to as a "switch position".

As shown in FIG. 2A, a part of the switch shaft 42 protrudes from the switch mounting hole provided in the cover 45 of the console device 4. The switch shaft 42 includes the first switch shaft 421 to which the switch cap 41 is attached, and the second switch shaft 422 that is integrally formed with the first switch shaft 421 and supports the first switch shaft 421.

FIG. 2B shows an example of a switch cap 41 without the switch shaft 42. FIG. 2B illustrates nine switch caps 41a to 41i.

The upper left switch cap 41a has a part operated by the user (hereinafter referred to as a knob) that has cylindrical shape. The switch cap 41a corresponds to, for example, an operation of rotating the cylindrical knob or tilting it up/down/left/right. The switch cap 41b has cylindrical knob having a diameter larger than that of the switch cap 41a. The switch cap 41b corresponds to, for example, an operation of rotating the knob or pressing an upper surface of the cylindrical knob. The switch cap 41c and the switch cap 41d have a protrusion of a substantially rectangular parallelepiped as the knob. This knob has a shape suitable for, for example, a 90-degree twist operation to the left and right. The switch cap 41e and the switch cap 41g have a substantially cylindrical knob with one end missing, and are suitable for, for example, a rotation operation. The missing end of the switch cap 41e and the switch cap 41g assist the user in recognizing the amount of rotation according to their positions. The switch cap 41f has a substantially cubic knob, and is suitable for, for example, an operation of pressing the knob. The switch cap 41i has a disc-shaped knob, and is suitable for, for example, an operation of pressing the knob.

The switch cap 41 in FIG. 2B is shown as an example, and the switch cap 41 may have a polygonal column knob or a T-shaped lever-shaped knob. The switch cap 41 may have any shape as long as it is detachable on the switch shaft 42.

The switch cap 41 is associated with one function of the X-ray diagnostic apparatus 100. There may be a plurality of types of switch caps 41 for one function. At least one switch cap 41 is provided for every function of the X-ray diagnostic apparatus.

The shape of the switch cap 41 is closely related to the operation of the switch 40. Thus, the function of the X-ray diagnostic apparatus 100 associated with the switch cap 41 is determined by the shape of the switch cap 41. When the operation of the operation target device 1 and the operation of the switch 40 are different, the intuitive operation of the switch 40 is hindered. For example, when the function of rotating the Ω arm or the C arm around the object S is associated with the switch cap 41 suitable for the operation of pressing the knob such as the switch cap 41i, the intuitive operation is hindered since the user cannot easily imagine in which direction the arm operates with respect to the operation of pressing the switch 40.

Meanwhile, when the switch cap 41 suitable for the operation of rotating the knob, such as the switch cap 41e and the switch cap 41g, is associated with the function of rotating the Ω arm and the C arm around the object S, the user can easily grasp the rotation direction and the amount of rotation, and intuitive operation becomes easy. Hence, it is preferable that the switch cap 41 is associated with each function of the X-ray diagnostic apparatus 100 suitable for the shape of the switch cap 41.

Further, a label such as a pictogram, a figure, or a character indicating a function associated with the switch cap 41 may be provided on the surface of the knob of each switch cap 41. With such labels, the user can easily select the switch cap 41 corresponding to the desired function from the plurality of switch caps 41.

Figure 3B:
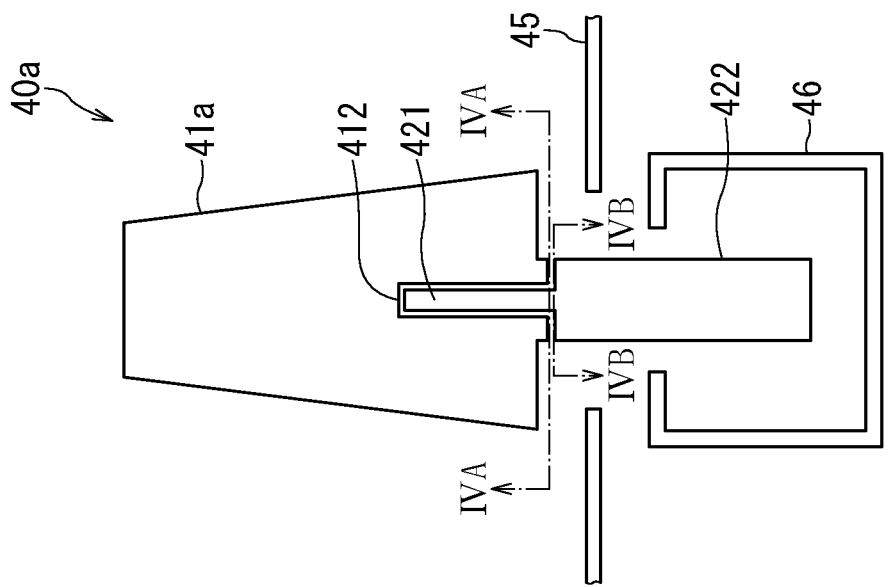
FIG. 3B is a sectional view taken along line IIIB-IIIB of the switch shown in the upper left of the console device shown in FIG. 3A.
Figure 3A:
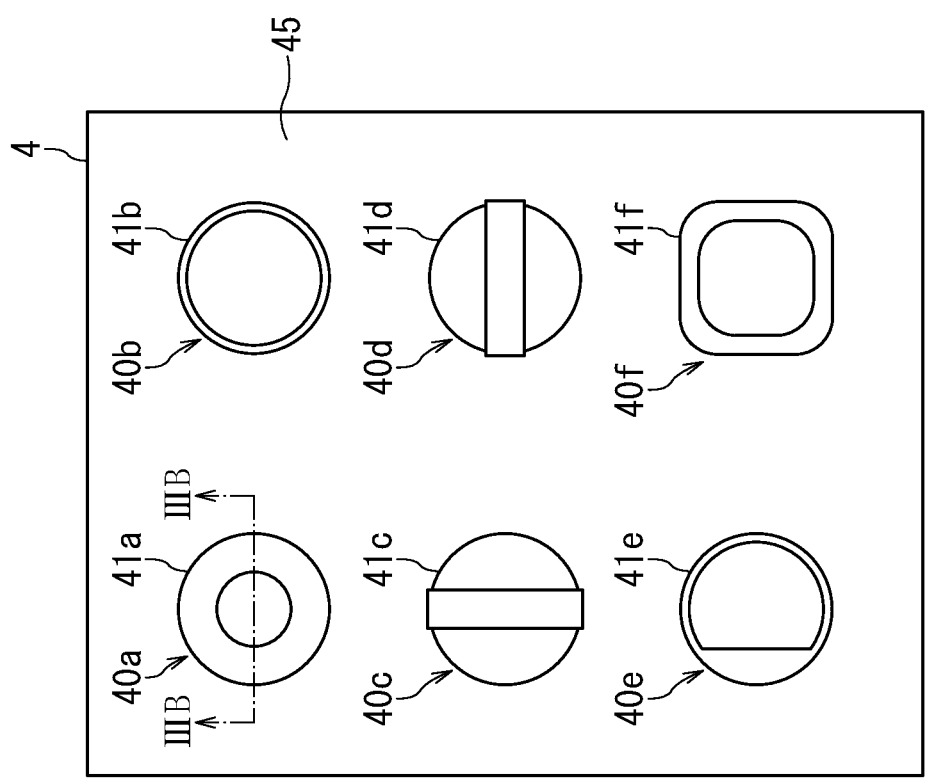
FIG. 3A is a front view showing an example of a console device to which a switch cap is attached.

FIG. 3 is a schematic diagram showing an example of the structure of the switch 40 of the X-ray diagnostic apparatus according to the first embodiment. FIG. 3A shows the console device 4 in which the six switch caps 41a to 41f selected from the switch caps 41a to 41i shown in FIG. 2B are attached to the corresponding six switch shafts 42a to 42f shown in FIG. 2A.

The internal structures of the switches 40a to 40f shown in FIG. 3A are all common. Each switch 40 can therefore generate a signal corresponding to the operation of the switch cap 41 regardless of which switch cap 41 is attached. For example, the internal structure of the switches 40a to 40f is composed of a multifunctional switch capable of accepting a plurality of types of operations. The multifunctional switch, for example, has internal contacts corresponding to a rotary encoder and a push button switch, and generates an output signal according to an operation on the switch such as rotation and pressing.

FIG. 3B schematically shows a cross section of IIIB-IIIB of the switch 40a shown in the upper left of the console device 4 of FIG. 3A.

As shown in FIG. 3B, the switch cap 41a of the switch 40a has a detachable portion 412. The detachable portion 412 is a vertical hole provided inside the switch cap 41a.

The switch shaft 42a has the first switch shaft 421 and the second switch shaft 422. The first switch shaft 421 is a portion protruding from the cover 45 of the console device 4. The first switch shaft 421 is inserted into the detachable portion 412 provided on the switch cap 41, whereby the switch cap 41 is attached to the switch shaft 42. The first switch shaft 421 is supported by the second switch shaft 422, and the bottom portion of the second switch shaft 422 is housed in the case 46.

The switch 40 may be provided with a fixing mechanism that prevents the switch cap 41 from detaching from the switch shaft 42. The fixing mechanism is provided on the switch cap 41, for example.

The fixing mechanism is, for example, a protruding portion provided at the bottom portion of the switch cap 41. The switch cap 41 may be fixed so as to be hooked by the cover 45 by inserting the protruding portion of the switch cap 41 under the cover 45. The fixing mechanism may have any configuration as long as it can prevent the switch cap 41 from detaching from the switch shaft 42.

FIG. 4 is a schematic sectional view showing an example of the recognition function provided on the switch of the console device 4 for the X-ray diagnostic apparatus according to the first embodiment. The upper figure of FIG. 4A shows the lower side surface of the switch cap 41a. The lower figure of FIG. 4A schematically shows the IVA-IVA cross section of FIG. 3B.

The lower figure of FIG. 4A schematically shows the bottom surface of the switch cap 41a. The bottom surface of the switch cap 41a has six identification information retention portions 413a to 413f. The identification information retention portions 413a to 413f are, for example, protruding portions. The switch cap 41 can have identification information depending on the combination of the protruding portions.

Specifically, the switch cap having only the identification information retention portion 413a and the switch cap having the identification information retention portion 413a and the identification information retention portion 413b have different identification information. The identification information that uniquely identifies the switch cap 41a can be obtained by making the number and arrangement of the protruding portions different. There are 64 (=2^6) combinations of the number and arrangement of the six protruding portions. Therefore, the switch cap 41 having a maximum of 64 different identification information can be fabricated by making the number and arrangement of the protruding portions different.

FIG. 4B schematically shows a cross section of IVB-IVB of FIG. 3B. That is, FIG. 4B shows the upper surface of the second switch shaft 422. The upper surface of the second switch shaft 422 is provided with a detection portion 423. The detection portion 423 includes the first detection portion 423a, the second detection portion 423b, the third detection portion 423c, the fourth detection portion 423d, the fifth detection portion 423e, and the sixth detection portion 423f. Each of the first detection portion 423a to the sixth detection portion 423f is a push button switch such as a momentary switch. As such, the detection portion 423 includes 6 switch elements.

When the switch cap 41a is attached to the first switch shaft 421, the bottom surface of the switch cap 41a and the upper surface of the second switch shaft 422 face each other. Therefore, when the switch cap 41a is attached to the first switch shaft 421, the protruding portions of the identification information retention portions 413a to 413f shown in the lower figure of FIG. 4A press the momentary switches of the first detection portion 423a to the sixth detection portion 423f shown in FIG. 4B, respectively. The number and arrangement of the protruding portions provided on the switch cap 41a are different for each switch cap 41, and the combination of the detection portion 423 pressed when the switch cap 41 is attached to the switch shaft 42 is different.

The signal detected by the detection portion 423 is transmitted to the processing circuitry of the console device 4, and the processing circuitry identifies the switch cap 41a based on the combination of the pressed detection portion 423.

FIG. 4 shows an example in which the detection portion 423 includes push button switch elements and the identification information retention portion 413 is a protruding portion for pressing the detection portion 423, but the present invention is not limited to this example. For example, the identification information retention portion 413 may be composed of at least one conductive pin, and the detection portion 423 may be composed of a plurality of contact portions in contact with the conductive pins. In this case, the switch cap 41a may be identified from a combination of electrical signals generated when conductive pins come into contact with contact portions. Further, the identification information retention portion 413 may be composed of a contactless IC (Integrated Circuit) or a two-dimensional bar code, and the identification information of the switch cap may be registered in the IC or the two-dimensional bar code. In this case, the detection portion 423 is composed of a reading member to read an information registered in the IC or the two-dimensional bar code. The detection portion 423 reads the identification information registered in the IC or the two-dimensional bar code, and the switch cap 41a is identified based on the identification information.

FIG. 4 illustrates an example of a case where the identification information retention portion 413 is provided on the bottom surface of the switch cap 41 and the detection portion 423 is provided on the upper surface of the second switch shaft 422. However, the positions of the identification information retention portion 413 and the detection portion 423 may be provided at any position of the switch 40 as long as they are provided so as to face each other. For example, the identification information retention portion 413 may be provided in the detachable portion 412 inside the switch cap 41, and the detection portion 423 may be provided in the first switch shaft 421.

Figure 5:
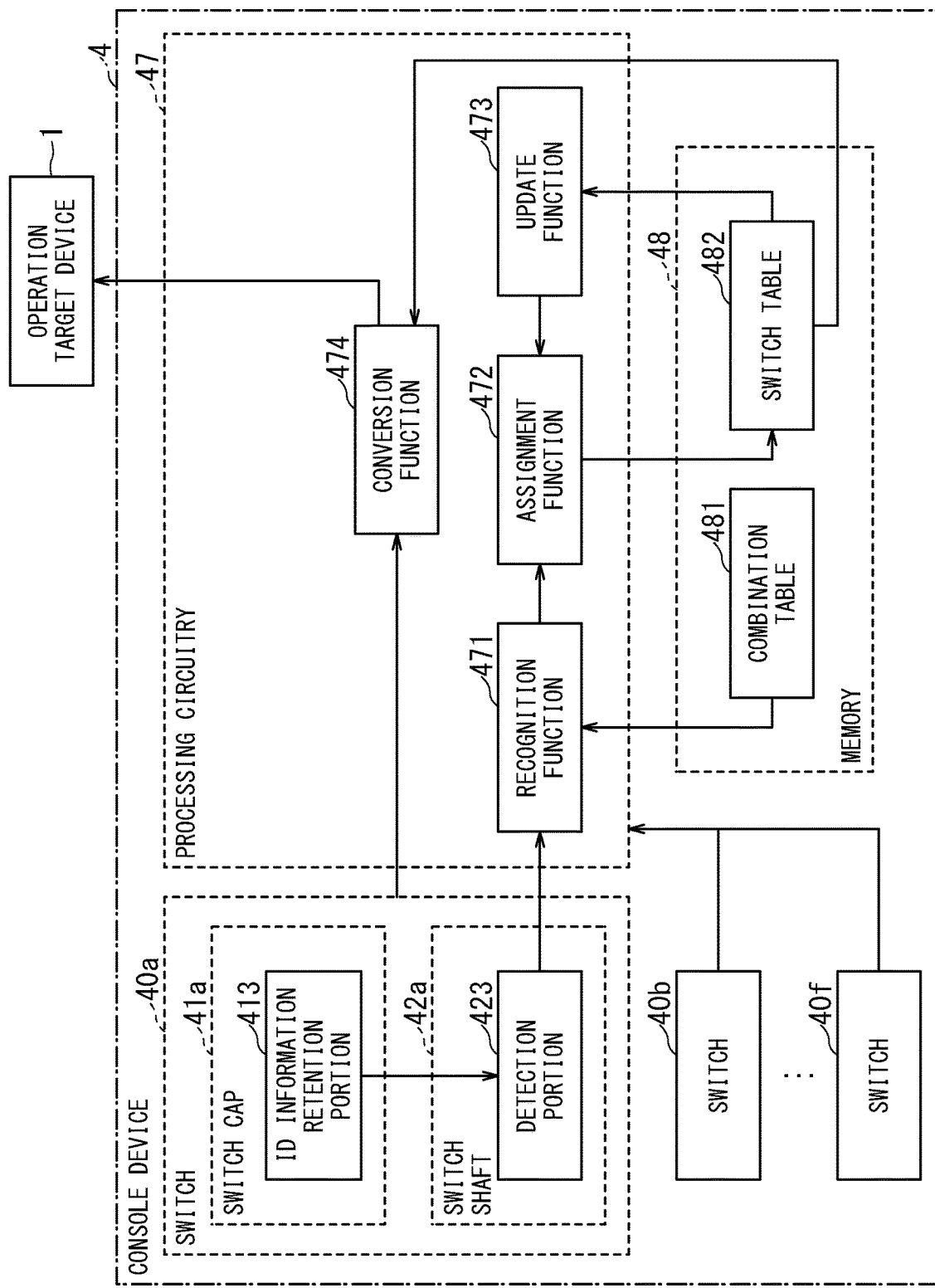
FIG. 5 is a functional block diagram showing an example of a functional configuration of the X-ray diagnostic apparatus according to the first embodiment.

FIG. 5 is a functional block diagram showing an example of a functional configuration example of the X-ray diagnostic apparatus 100 according to the first embodiment. FIG. 5 describes a console device 4 having six switches 40a to 40f as an example.

As shown in FIG. 5, the console device 4 includes six switches 40a to 40f. The operation signals from the switches 40a to 40f are input to the processing circuitry 47.

The switch 40a has the switch cap 41a and the switch shaft 42a. The switch cap 41a has the identification information retention portion 413, and the switch shaft 42a has the detection portion 423 that detects the identification information retention portion 413. The information detected by the detection portion 423 is transmitted to the processing circuitry 47 of the console device 4.

The console device 4 has processing circuitry 47 and memory 48. The processing circuitry 47 includes a processor. The processor of the processing circuitry 47 executes the recognition function 471, the assignment function 472, the update function 473, and the conversion function 474 by executing the program stored in the memory 48.

The recognition function 471 identifies a function assigned to the switch 40 based on the information detected by the detection portion 423.

The assignment function 472 assigns a function to the switch 40a based on the type of the switch cap 41. The assignment function 472 assigns the function identified by the recognition function 471 to the switch 40 to which the switch cap 41 is attached.

The update function 473 sends an instruction to update the function already assigned to the switches 40a to 40f to the assignment function 472. The instruction to update may be transmitted, for example, when the power is turned on to the X-ray diagnostic apparatus 100. Further, the instruction to update may be transmitted to the assignment function 472 at the timing before the start of the examination of the X-ray diagnostic apparatus 100. The update function 473 may refer to the examination information to determine whether the state of the X-ray diagnostic apparatus is before the examination. Further, the instruction to update may be transmitted to the assignment function 472 at the timing when the user inputs the instruction to update via the input device such as the console device 4 or the input circuit.

The conversion function 474 converts the signal generated by the operation performed by the user on the switch 40 into a signal corresponding to the function assigned to the switch 40 which the user operated. That is, the conversion function 474 converts the signal generated by the switch 40 into the drive signal of the operation target device 1 operated (driven) by the switch 40.

Memory 48 has the combination table 481 and the switch table 482. The memory 48 has a configuration including a storage medium that can be read by a processor, such as a magnetic or optical recording medium or a semiconductor memory. A part or all of the program and data in the storage medium of the memory 48 may be downloaded by communication via an electronic network, or may be given to the memory 48 via a portable storage medium such as an optical disk. A part or all of the information stored in the memory 48 is distributed and stored or duplicated in at least one of a storage medium such as an external memory or another memory of the X-ray diagnostic apparatus 100 (not shown).

The processing circuitry 47 and memory 48 may be provided in the control device of the X-ray diagnostic apparatus 100. In this case, the identification information of the switch cap 41 detected by the detection portion 423 of the switch 40 is transmitted to the control device of the X-ray diagnostic apparatus 100 wirelessly or by wire.

The combination table 481 is a table in which the identification information of the switch cap 41 and the function corresponding to the identification information are associated with each other.

The switch table 482 is a table in which the position of the switch 40 and the function assigned to the switch 40 are associated with each other.

(2) Operation

Next, the operation of the X-ray diagnostic apparatus 100 and the console device 4 for the X-ray diagnostic apparatus will be described.

Figure 6:
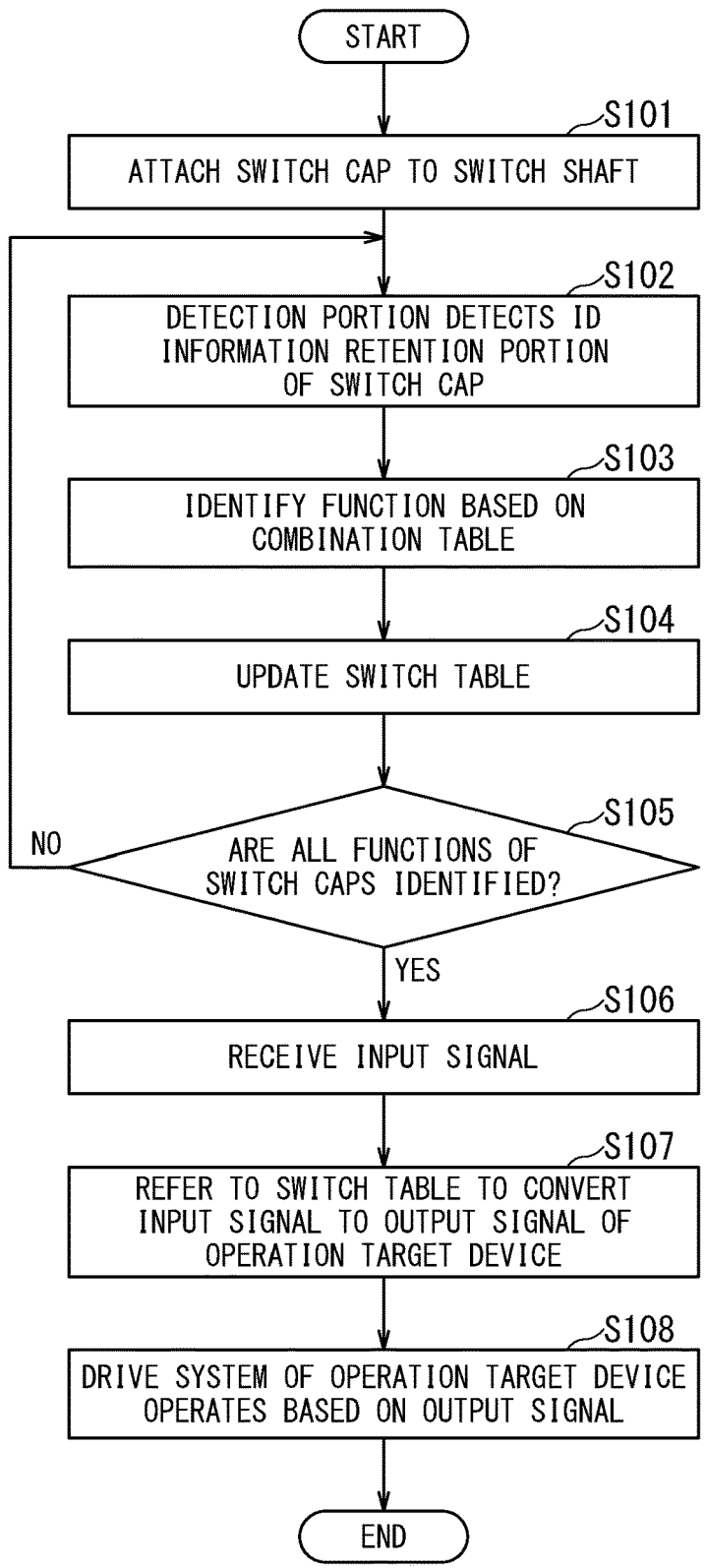
FIG. 6 is a flowchart showing an example of the operation of the X-ray diagnostic apparatus according to the first embodiment.

FIG. 6 is a flowchart showing an example of the operation of the X-ray diagnostic apparatus 100 according to the first embodiment. The reference character with "S" followed by a number denotes each step of the flowchart. In FIG. 6, the console device 4 including the six switches 40 illustrated in FIG. 3 will be described as an example.

In step S101, the switch caps 41a to 41f are attached to the switch shafts 42a to 42f, respectively (see FIG. 3A). The user may input the instruction to update via the input circuit before or after the replacement of the switch cap 41.

In step S102, the detection portion 423 provided on the second switch shaft 422 detects the identification information retention portion 413 provided on the switch cap 41. Hereinafter, the switch 40a exemplified in FIG. 4, in which the detection portion 423 is composed of six momentary switches, will be described as an example.

The switch cap 41a attached to the switch shaft 42a has six protruding portions as the identification information retention portion 413. The switch shaft 42a is provided with six momentary switches as the detection portion 423. Therefore, when the switch cap 41a is attached to the switch shaft 42a, all the momentary switches, i.e., the first detection portion 423a to the sixth detection portion 423f, are pressed. The signals generated in the first detection portion 423a to the sixth detection portion 423f are transmitted to the recognition function 471.

In step S103, the recognition function 471 identifies the function registered in the switch cap 41a with reference to the combination table 481. The function identified by the recognition function 471 is transmitted to the assignment function 472.

FIG. 7 is a table showing an example of the combination table of the X-ray diagnostic apparatus 100 according to the first embodiment. The first line of FIG. 7 shows the first detection portion 423a to the sixth detection portion 423f. The first column of FIG. 7 shows the functions 1 to 64 registered in the switch cap 41. In the table, "ON" indicates the state in which the momentary switch is pressed by the protruding portion of the identification information retention portion 413 and a signal is generated, and "OFF" indicates the state in which the momentary switch is not pressed by the protruding portion of the identification information retention portion 413 and the signal is not generated.

When the switch cap 41a is attached to the switch shaft 42a, an "ON" signal is transmitted to the recognition function 471 from all the momentary switches of the first detection portion 423a to the sixth detection portion 423f. The recognition function 471 refers to the combination table 481 and searches for rows in which the first detection portion 423a to the sixth detection portion 423f are "ON". The row in which the first detection portion 423a to the sixth detection portion 423f are "ON" is the second row of the combination table 481. The function of the second row of the combination table 481 is "function 1". Accordingly, the recognition function 471 identifies that the function associated with the switch cap 41a is the "function 1".

When another switch cap 41 is attached to the switch shaft 42, the signals from the momentary switches of the first detection portion 423a to the sixth detection portion 423f are sequentially "ON", "ON", "ON", "ON", "OFF", and "OFF". This combination of signals corresponds to the fourth row of the combination table 481. Accordingly, the recognition function 471 identifies that the function associated with the switch cap 41 is "function 3" when such a signal is input.

Return to FIG. 6 and continue the explanation of the flowchart.

In step S104, the assignment function 472 updates the switch table 482 based on the function identified by the recognition function 471. The assignment function 472 may confirm the reception of the instruction to update before updating the switch table 482. If there is no instruction, the assignment function 472 ends the process without updating the switch table 482. It is possible to prevent the function of the switch 40 from being erroneously changed by updating the switch table 482 only when the instruction to update is received. The update function 473 may determine the update timing and sends the instruction to update to the assignment function 472 so that the function of the switch 40 is not changed during the examination.

FIG. 8 is a table showing an example of the switch table 482 of the X-ray diagnostic apparatus 100 according to the first embodiment. The left column of FIG. 8 shows the switch position, and the right column of FIG. 8 shows the function assigned to the switch position.

For example, in the console device 4 shown in FIG. 3A, the switch position is "position 1" on the left of the first row, "position 2" on the right of the first row, "position 3" on the left of the second row, "position 4" on the right of the second row, "position 5" on the left of the third row, and "position 6" on the right of the third row. In step S103, the function identified by the recognition function 471 as the function associated with the switch cap 41a is "function 1". The switch cap 41a is attached to the "position 1". Hence, the assignment function 472 registers "function 1" as a function assigned to "position 1".

When the function of the switch cap 41 cannot be identified, the assignment function 472 may assign the same function as the previously assigned function without updating the switch table 482. For example, when the identification information of the switch cap 41 cannot be recognized correctly, or when the function is not registered yet in the combination table 481, the assignment function 472 stops updating the switch table 482. This makes it possible to prevent the function of the switch 40 from being erroneously changed.

When the function of the switch cap 41 cannot be identified by the recognition function 471, the switch 40 to which the switch cap 41 whose function cannot be identified is attached may be disabled. That is, when the function of the switch cap 41 cannot be identified, the function may not be assigned to the switch 40. Further, when the function of the switch cap 41 cannot be identified by the recognition function 471, the user may be notified to that effect. For example, a message indicating that the function is not recognized may be displayed on the display 29 together with the switch position.

Return to FIG. 6 again and continue the explanation of the flowchart.

In step S105, the recognition function 471 determines whether all the functions of the switch caps 41 attached to the switch shafts 42a to 42f have been identified. When the functions of all the attached switch caps 41 are not identified, the process branches to NO of step S105, returns to step S102, and the processes of steps S102 to S105 are repeated. Meanwhile, when the functions of all the attached switch caps 41 are identified, the process branches to YES of step S105 and proceeds to step S106.

In step S106, the switch 40 is operated by the user, and the conversion function 474 receives the input signal from the switch 40 operated by the user.

In step S107, the conversion function 474 refers to the switch table 482 and converts the input signal into the output signal of the operation target device 1.

In step S108, the conversion function 474 transmits the output signal to the operation target device 1, and the operation target device 1 operates the drive system of the operation target device 1 based on the output signal.

The explanation of the flowchart is as described above.

The console device 4 for the X-ray diagnostic apparatus 100 and the X-ray diagnostic apparatus 100 according to the first embodiment can easily change the function assigned to the switch 40 by simply changing the switch cap 41. Therefore, the user can freely customize the switch arrangement for each examination and each surgery.

It is assumed that the operation of the X-ray diagnostic apparatus 100 differs depending on conditions such as the clinical department, examination target, and surgical method. With the console device 4 according to the first embodiment, the console device 4 suitable for the examination and the surgery to be performed can be prepared by simply changing the arrangement of the switch cap 41 before the examination and the surgery.

Further, in the conventional console device, when a plurality of users use the console device 4 at the same time, the switches used by each user are arranged dispersedly on the console device. Thus, the hands of the users have to cross each other when using the switch, or each user has to move to the position where the desired switch to be operated for each user is located. According to the console device 4 according to the first embodiment, the switches 40 used by the user can be collectively arranged according to the standing position of the user.

By arranging the switch 40 for each user, the switch used by the surgeon in the surgery and the switch used by the assistant can be separated, and the switch can be used cleanly and safely.

Also, conventionally, when a new function is provided to the X-ray diagnostic apparatus 100, the new function is executed by combining switches to which other functions are already assigned. Hence, it was not possible to operate the switch intuitively suitable for the new function. According to the X-ray diagnostic apparatus 100 and the console device 4 for the X-ray diagnostic apparatus 100 according to the first embodiment, when a new function is added to the X-ray diagnostic apparatus 100, by providing the new switch cap 41 suitable for the new function along with changing the program for the new function, the switch that is dedicated to the new function and is capable of intuitive operation can be easily provided.

Although the switch 40 provided on the console device 4 has been described as an example in the first embodiment, the switch 40 is not limited to the switch 40 provided on the console device 4. For example, the foot switch 5 can be provided with the switch 40 described in the first embodiment. Further, the first embodiment can be applied to all the switches 40 included in the X-ray diagnostic apparatus 100, such as the switches included in the operation panel provided on the C arm and/or the bed device 3.

Further, in the first embodiment, an example is shown in which all six switches 40 provided on the console device 4 can be replaced, only a part of the switches 40 included in the console device 4 and the X-ray diagnostic apparatus 100 may be configured by the switch 40 described in the first embodiment.

As described above, according to the X-ray diagnostic apparatus 100 and the console device 4 for the X-ray diagnostic apparatus 100 according to the first embodiment, the function assigned to each switch 40 can be easily changed by simply replacing the switch cap 41. Accordingly, the user can arrange the switch corresponding to the desired shape or operation at the desired position.

Second Embodiment

In the first embodiment, the console device 4 for the X-ray diagnostic apparatus 100 and the X-ray diagnostic apparatus 100 in which the switch cap 41 is detachable has been described. However, the detachable configuration is not limited to the switch cap 41. A second embodiment relates to the X-ray diagnostic apparatus 100 and the console device 4 for the X-ray diagnostic apparatus 100 in which the switch shaft 42 is detachable in addition to the switch cap 41.

Figure 9B:
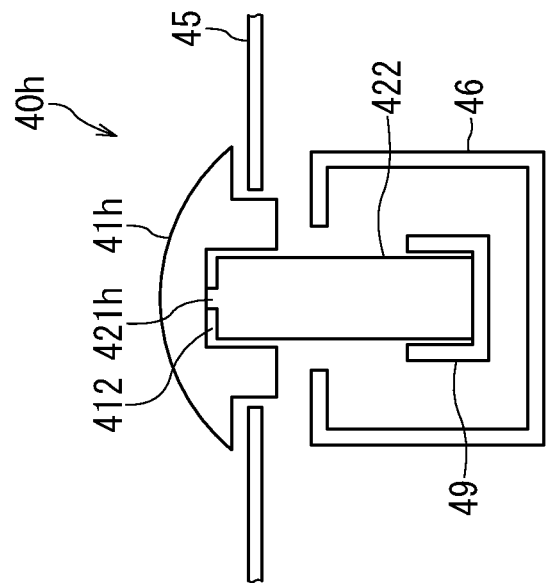
FIG. 9B is a sectional view showing another example of the switch of the X-ray diagnostic apparatus according to the second embodiment.
Figure 9A:
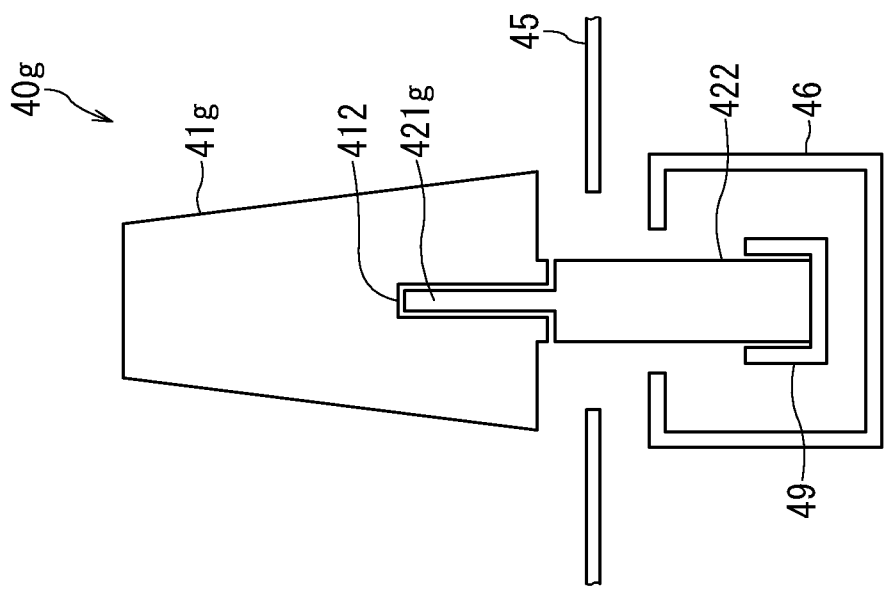
FIG. 9A is a sectional view showing an example of the switch of the X-ray diagnostic apparatus according to the second embodiment.

FIG. 9 is a schematic sectional view showing an example of the structure of the switch 40 of the X-ray diagnostic apparatus 100 according to the second embodiment. The switch 40g shown in FIG. 9A is attached with the switch cap 41g having a knob of the same shape as the switch cap 41a shown in FIG. 3B. The switch cap 41g is a switch cap suitable for rotation operation. Meanwhile, the switch 40h in FIG. 9B is attached with the switch cap 41h which has a disk-shaped knob and is suitable for a pressing operation.

For example, when the switch cap 41g shown in FIG. 9A is replaced with the switch cap 41h shown in FIG. 9B, the switch cap 41h is attached to the tip of the first switch shaft 421g. Thus, the knob suitable for the pressing operation is located higher than the cover 45. When the switch cap 41g suitable for pressing is attached at a high position with respect to the cover 45, it is difficult for the user to recognize the switch 40h suitable for pressing. Further, since the switch cap 41h is attached to the tip of the first switch shaft 421, it may be mistaken for a lever-type switch.

Therefore, by changing the switch shaft 421g to the switch shaft 421h shorter than the switch shaft 421g, it is possible to provide a switch 40h having a height suitable for the switch cap 41h as shown in FIG. 9B.

As described above, in the second embodiment, the length of the first switch shaft 421 can be changed to the length suitable for the shape of the switch cap 41 by making the switch shaft 42 detachable together with the switch cap 41. For example, in the case of a switch suitable for rotation operation such as the switch 40g, the longer the first switch shaft 421 is, the easier it is to operate. Meanwhile, in the case of a switch suitable for a push operation such as the switch 40h, the shorter length of the first switch shaft 421 makes it easier push the knob, and the user can easily recognize that it is a push button switch.

The second embodiment has the same configuration as the first embodiment except that the switch shaft 42 is detachable. Therefore, the second embodiment has the same effect as the first embodiment.

Further, in the second embodiment, since the length of the first switch shaft 421 can be changed according to the shape of the switch cap 41, the height of the switch 40 can be adjusted in various ways. Hence, it is possible to increase the types of switches.

Although an example in which the switch cap 41 and the switch shaft 42 are separately attached and detached is described above, the switch cap 41 and the switch shaft 42 may be integrated and made detachable.

In this case, the identification information retention portion 413 may be provided on the bottom surface of the second switch shaft 422 supported by the bearing 49 housed in the case 46, and the detection portion 423 may be provided on the surface of the bearing 49 that opposes the identification information retention portion 413. With this configuration, a member in which the switch cap 41g and the switch shaft 42 are integrated may be recognized.

It is possible to provide the console device 4 having excellent robustness and waterproofness by integrating the switch cap 41 and the switch shaft 42 into a detachable device.

In the console device 4 for the X-ray diagnostic apparatus 100 and the X-ray diagnostic apparatus 100 of the first and second embodiments, an example in which the function associated with the switch cap 41 is automatically assigned to the switch 40 has been described. However, the user may manually assign the function to the switch 40 after replacing the switch cap 41.

For example, a function may be assigned to the switch cap 41 by using a DIP switch (Dual Inline Package switch) mounted on the electronic circuit board of the console device 4. Further, a software for assigning the function of the switch 40 to the console device 4 for the X-ray diagnostic apparatus 100 or the X-ray diagnostic apparatus 100 may be implemented, or the switch table 482 may be displayed on a display device such as display 29 and the function assignment to the switch 40 may be manually updated by the user.

Third Embodiment

A third embodiment relates to the X-ray diagnostic apparatus 100 and the console device 4 for the X-ray diagnostic apparatus 100, which are provided with the suppression mechanism 415 on the switch cap 41 that suppresses operations other than operations corresponding to (suitable for) the function assigned to the switch 40.

Some switches 40 can accept a plurality of types of operations. For example, the switch 40a shown in FIG. 3B can accept a pressing operation in addition to a rotating operation. The operations that the switch 40 can accept are diverse. Meanwhile, the types of the operations of the operation target device 1 may be less than the operation that the switch 40 can accept.

For example, with respect to the switch 40 that can be operated in four directions of up/down/left/right, when the operation of the operation target device 1 is assigned only to the operation of the switch 40 in the up/down direction, a state in which no operation is executed may occur because the user can operate the switch 40 in the left-right direction to which no operation is assigned. In this case, when the operation target device 1 does not operate even though the user operates the switch 40, the user suspects a failure and must confirm whether the X-ray diagnostic apparatus 100 has an abnormality.

Further, when the operation of the operation target device 1 cannot be confirmed from the outside, the user misunderstands that the operation is accepted by the switch 40 and the operation of the operation target device 1 is completed, and thus, there is a possibility that imaging will start under conditions different from the determined imaging conditions.

In order to solve the above problems, the X-ray diagnostic apparatus 100 and the console device 4 for the X-ray diagnostic apparatus 100 according to the third embodiment include the suppression mechanism 415 that suppresses operations other than the operations corresponding to (suitable for) the functions assigned to the switch 40 on the switch cap 41.

Figure 10A:
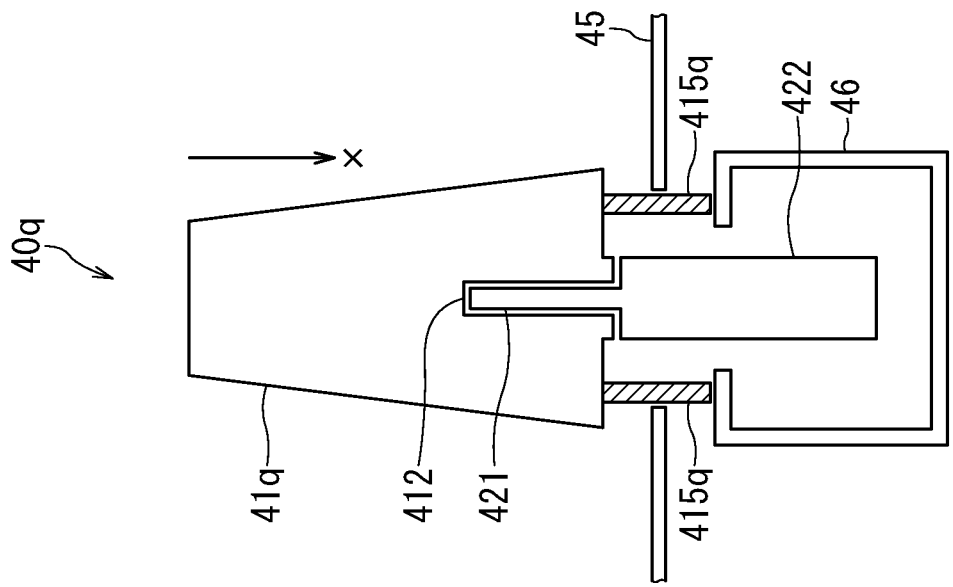
FIG. 10A is a sectional view showing an example of the suppression mechanism of the switch of the X-ray diagnostic apparatus according to the third embodiment.

FIG. 10 is a schematic sectional view showing an example of the suppression mechanism of the switch of the X-ray diagnostic apparatus 100 according to the third embodiment. FIG. 10A is a schematic sectional view of the switch 40p having the suppression mechanism 415p that suppresses the operation of tilting the switch cap 41p to the left and right.

As shown in FIG. 10A, the switch cap 41p has two suppression mechanisms 415p on the left and right that extend in parallel with the switch shaft 42 at the bottom of the switch cap 41p. When the switch cap 41p is attached to the switch shaft 42, each of the suppression mechanisms 415p is inserted between the case 46 and the second switch shaft 422. When the switch cap 41p is to be tilted to the left, the suppression mechanisms 415p, that are integrated with the switch cap 41p and are sandwiched between the case 46 and the second switch shaft 422, hinder the tilt of the switch cap 41p. The same applies when the switch cap 41p is to be tilted to the right. Therefore, the user cannot tilt the switch shaft 42 to the left or right, and the operation of tilting the switch 40p to the left or right cannot be input. Meanwhile, there is no suppression mechanism 415p in the up/down direction of the switch shaft 42 (in the front-back direction with respect to the paper surface), and the switch shaft 42 can be tilted up and down. In addition, although FIG. 10A shows an example of suppressing the inclination in the left-right direction, the present invention is not limited to this example. the suppression mechanisms 415p may be provided in the up/down direction of the switch shaft 42 such that an operation in the left/right direction can be input while suppressing the tilt of the switch shaft 42 in the up/down direction.

Figure 10B:
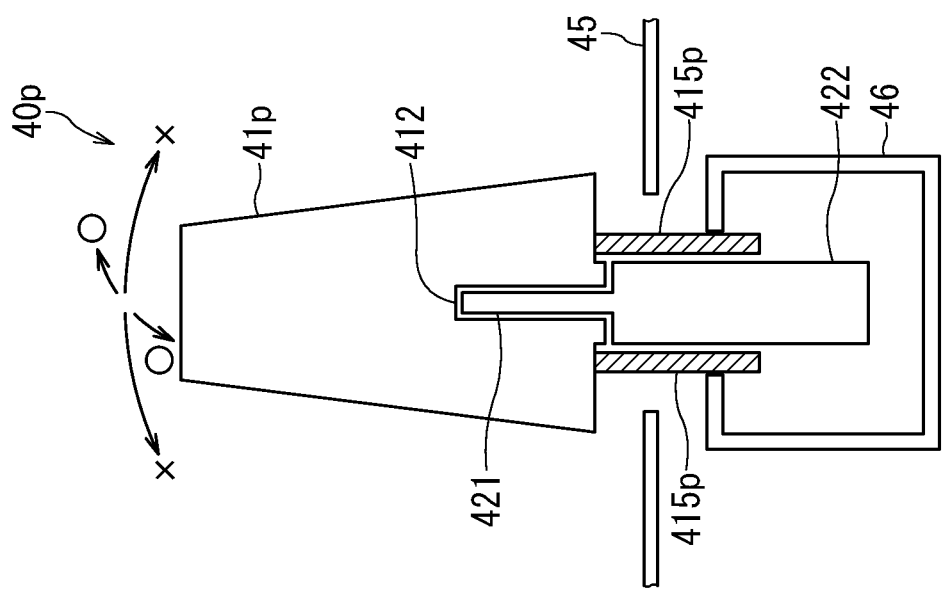
FIG. 10B is a sectional view showing another example of the suppression mechanism of the switch of the X-ray diagnostic apparatus according to the third embodiment.

FIG. 10B schematically shows a sectional view of the switch 40q having the suppression mechanism 415q that suppresses the pressing of the switch cap 41q. As shown in FIG. 10B, the switch cap 41q has two suppression mechanisms 415q extending parallel to the switch shaft 42 at the bottom of the switch cap 41q. Each of the suppression mechanisms 415q is in contact with the case 46. When the switch cap 41q is pressed, the suppression mechanisms 415q come into contact with the case 46 and stop, whereby the switch cap 41q is not pressed.

FIG. 11 is a schematic sectional view showing an example of the rotation suppression mechanism of the switch of the X-ray diagnostic apparatus 100 according to the third embodiment. FIG. 11A is a schematic sectional view of the switch 40r in the long axis direction. FIG. 11B is a sectional view taken along line XIB-XIB of the switch 40r of FIG. 11A.

As shown in FIG. 11B, the circumference of the first switch shaft 421 is covered with the annular second switch shaft 422. The second switch shaft 422 is fixed, while the first switch shaft 421 rotates. When the user rotates the switch cap 41r attached to the first switch shaft 421, the first switch shaft 421 rotates integrally with the switch cap 41r, and the rotation operation is input to the switch 40r.

As shown in FIGS. 11A and 11B, the suppression mechanism 415r provided at the bottom of the switch cap 41r extends in parallel with the second switch shaft 422, and is inserted into the recess 425r provided in the second switch shaft 422. When the switch cap 41r is to be rotated, the suppression mechanism 415r inserted into the recess 425r provided in the second switch shaft 422 hinders the rotation of the switch cap 41r. Hence, the first switch shaft 421 does not rotate, and the rotation operation is not input to the switch 40r.

Although FIG. 11 shows an example in which the recess 425r is provided on the second switch shaft 422, the recess 425r may be provided on both the first switch shaft 421 and the second switch shaft 422. In this case, the suppression mechanism 415r is inserted into both the first switch shaft 421 and the second switch shaft 422.

Further, the recess 425r may be a vertical hole provided so as to penetrate the upper part of the case 46. In this case, the rotation of the switch cap 41r can be suppressed by inserting the suppression mechanism 415r into the vertical hole. Meanwhile, when the switch cap 41r is pressed, the suppression mechanism 415r can slide in the vertical hole in the vertical direction, whereby the pressing operation is possible. Further, since the suppression mechanism 415r is inserted into the vertical hole provided in the case 46, the suppression mechanism 415r hinders the movement of the switch cap 41r when the switch cap 41r is tilted to the left. Therefore, the operation of tilting the switch shaft 42 to the left can be suppressed by using the vertical hole.

In FIGS. 10 and 11, an example of the suppression mechanism 415 that suppresses the tilt operation, the pressing operation, and the rotating operation has been described. These suppression mechanisms 415 may be combined depending on the function associated with the switch cap 41. For example, in the case of accepting only the operation of tilting the switch 40 up and down, the switch 40 may be provided with the suppression mechanism 415p that suppresses the operation of tilting the switch 40 left and right, the suppression mechanism 415q that suppresses the pressing of the switch 40, and the suppression mechanism 415r that suppresses the rotation of the switch 40. With such a configuration, it is possible to provide a switch 40 that can only accept an operation of tilting the switch 40 up and down.

The switch cap 41 having the suppression mechanism 415 may be provided with the identification information retention portion 413 and the detection portion 423 described in the first and second embodiments.

As described above, according to the console device 4 for the X-ray diagnostic apparatus 100 and the X-ray diagnostic apparatus 100 according to the third embodiment, in addition to the same effects as those of the first and second embodiments, it is further possible to prevent the switch 40 from being erroneously operated since the switch cap 41 has the suppression mechanism 415 as described above.

According to at least one embodiment described above, the switch can be freely customized.

Fourth Embodiment

The first embodiment can also be applied to automatic recognition of accessories that is used together with the console device 4 for the X-ray diagnostic apparatus 100 and the X-ray diagnostic apparatus 100 and is attached to and detached from the console device 4 for the X-ray diagnostic apparatus 100 and the X-ray diagnostic apparatus 100.

The fourth embodiment relates to a recognition function of the accessories.

Figure 12:
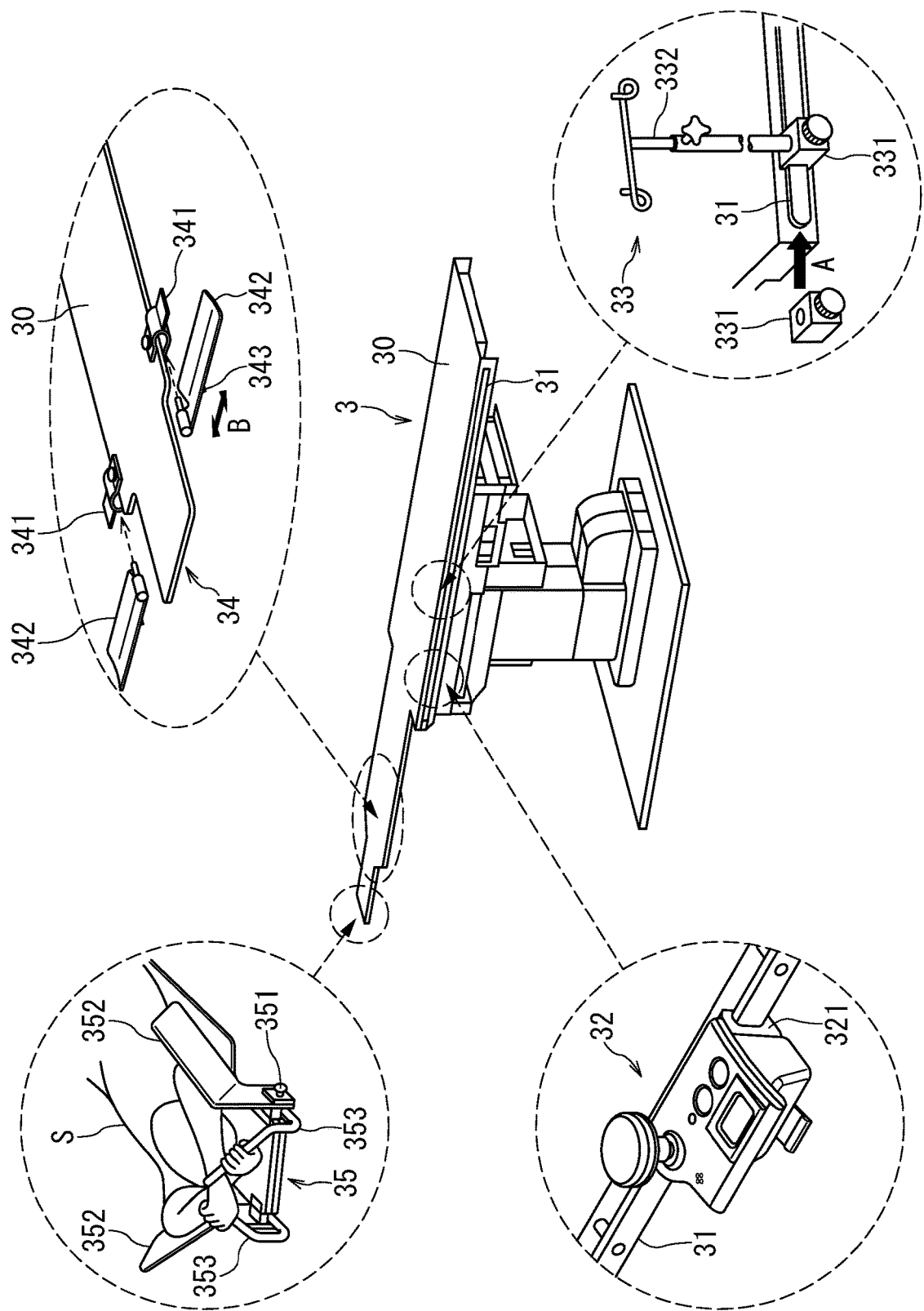
FIG. 12 is a schematic diagram illustrating accessories attached to the X-ray diagnostic apparatus according to the fourth embodiment.

FIG. 12 is a schematic diagram illustrating accessories attached to the X-ray diagnostic apparatus 100 according to the fourth embodiment. FIG. 12 shows an example of accessories attached to the tabletop 30 of the bed device 3 and the accessory attachment rail 31. The accessory attachment rail 31 is an example of an attachment portion.

The accessory shown in the lower left of FIG. 12 is a console device 32 for operating the tabletop. The console device 32 for operating the tabletop is attached on the accessory attachment rail 31 via the attachment hook 321. The console device 32 for operating the tabletop has the switch 40 for controlling the horizontal movement of the tabletop 30 and the raising and lowering of the tabletop 30. The attachment hook 321 can translate the accessory attachment rail 31 in the Z-axis direction. The user can install the console device 32 for operating the tabletop attached on the attachment hook 321 at a desired position in the Z-axis direction of the tabletop 30.

The accessory at the lower right of FIG. 12 is the infusion stand 33. The infusion stand 33 has the fixture 331 and the stand 332. An infusion bag is suspended on the stand 332. The stand 332 is supported by the fixture 331 attached on the accessory attachment rail 31. The fixture 331 is inserted in the direction of arrow A from one end of the accessory attachment rail 31 to be attached thereto. Further, the fixture 331 can translate the accessory attachment rail 31 in the Z-axis direction. The user can adjust the position of the infusion bag by moving the fixture 331 in the Z-axis direction of the tabletop 30 according to the position where the object S is placed.

The accessory on the upper left of FIG. 12 is the hand grip 35 attached to the tabletop 30. The hand grip 35 has the adjusting knob 351, the arm holder 352, and the grip 353. The hand grip 35 is used, for example, to prevent the object S from falling from the tabletop 30 by the object S gripping the grip 353 when the tabletop 30 is tilted with respect to the floor of the examination room for imaging. The arm holder 352 is a member that supports the arm of the object S that grips the grip 353. The angle between the arm holder 352 and the tabletop 30 can be adjusted by the adjusting knob 351.

The accessory on the upper right of FIG. 12 is the armrest 34 attached to the tabletop 30. The armrest 34 is used, for example, to keep the arm of object S out of the way during surgery. The armrest 34 has the holder 341, the armrest plate 342, and the angle adjusting shaft 343. The armrest plate 342 has a protrusion, and the protrusion is inserted into the holder 341 attached on and fixed to the tabletop 30. The angle between the armrest plate 342 and the side surface of the tabletop 30 can be adjusted by moving the angle adjusting shaft 343 provided on the armrest plate 342 in the direction of the arrow B.

Hereinafter, the fourth embodiment will be described by taking the console device 32 for operating the tabletop as an example.

The attachment hook 321 has the detection portion 423 described in the first embodiment. The console device 32 for operating the tabletop has the identification information retention portion 413 described in the first embodiment. When the console device 32 for operating the tabletop is attached to the attachment hook 321, the detection portion 423 detects the identification information retention portion 413, and the detected identification information is transmitted to the processing circuitry of the control device of the X-ray diagnostic apparatus 100. Each accessory has different identification information, and the X-ray diagnostic apparatus 100 automatically recognizes the attached accessory based on the identification information.

The accessory attachment rail 31 may be provided with the detection portion 423, and the attachment hook 321 may be provided with the identification information retention portion 413. For example, the detection portion 423 may be provided at one end of the accessory attachment rail 31. In this case, after the console device 32 for operating the tabletop is attached to said one end where the detection portion 423 is provided and is recognized by the X-ray diagnostic apparatus 100, the position of the console device 32 may be changed by sliding the console device 32 on the accessory attachment rail 31.

Further, a linear encoder may be provided on the attachment hook 321, and position information indicating at which position of the accessory attachment rail 31 the attachment hook 321 is placed may be transmitted to the X-ray diagnostic apparatus 100.

Accessories having different members on the left and right, such as the armrest plate 342 and the grip 353, may be provided with different identification information retention portion 413 such that the right one and the left one can be recognized independently.

The accessories used together with the X-ray diagnostic apparatus 100 are not limited to the accessories shown in FIG. 12. The tabletop 30 may be attached with accessories such as a footrest and a headrest. In addition, an automatic contrast medium injection device used when a contrast medium is administered to object S to image a blood vessel or a tumor may also be included in the accessories.

As described above, the fourth embodiment can be applied to any accessory as long as it is used together with the X-ray diagnostic apparatus 100 and is detachable to the X-ray diagnostic apparatus 100.

The console device 4 may be used as a single console device 4 by connecting a plurality of console devices. For example, the console device 4 may be separated into console devices for each of a plurality of operation target devices 1, such as a console device for the bed device 3, a console device for the imaging device 2, and the like. In this case, for example, the separable console device may be provided with the identification information retention portion 413, and the detection portion 423 may be provided on the stand 23. The identification information detected in the detection portion 423 may be processed by the processing circuitry of each console device or the processing circuitry of the control device of the X-ray diagnostic apparatus 100.

According to the X-ray diagnostic apparatus 100 and the console device 4 for the X-ray diagnostic apparatus 100 of the fourth embodiment, there is no need to make settings after the accessories are attached since the attached accessories are automatically recognized. Further, since the necessary accessories are determined according to examination and surgery, it is possible to check whether the accessories necessary for the examination and surgery are attached and notify the user of the check result.

According to at least one embodiment described above, the switch can be freely customized.

The term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising:
   a switch including a detachable grip portion; and
   processing circuitry configured to assign a function to the switch based on a type of the grip portion.

2. The medical image diagnostic apparatus according to claim 1, further comprising:
   a retention portion provided on the grip portion and retaining a function associated with the grip portion; and
   a detection portion detecting the retention portion of the grip portion attached to the switch,
   wherein the processing circuitry is configured to identify the function of the switch based on the information detected by the detection portion, and to assign the identified function to the switch.

3. The medical image diagnostic apparatus according to claim 2, wherein:
   the retention portion includes at least one protruding portion;
   the detection portion includes multiple switch elements; and
   the processing circuitry is configured to identify the function of the switch based on a combination of the multiple switch portions pressed by the at least one protruding portion.

4. The medical image diagnostic apparatus according to claim 2, wherein:
   the retention portion includes at least one conductive pin;
   the detection portion includes a plurality of contact portions; and
   the processing circuitry is configured to identify the function of the switch based on a combination of electrical signals generated by contact between the at least one conductive pin and the plurality of contact portions.

5. The medical image diagnostic apparatus according to claim 2, wherein
   the retention portion retains identification information of the grip portion;
   the detection portion detects the identification information registered in the retention portion; and
   the processing circuitry is configured to identify the function of the switch based on the identification information detected by the detection portion.

6. The medical image diagnostic apparatus according to claim 2, further comprising a plurality of switch shafts of different lengths that accept an operation to the switch,
   wherein each of the switch shafts is detachably attached to the switch according to the type of grip portion.

7. The medical image diagnostic apparatus according to claim 6, further comprising a bearing supporting the each of the switch shafts, wherein:
   the retention portion is provided on the each of the switch shafts, and the each of the switch shafts is detachably attached to the corresponding bearing together with the grip portion; and
   the bearing includes the detection portion.

8. The medical image diagnostic apparatus according to claim 1, wherein
   the processing circuitry is configured to assign the function identified based on the grip portion to the medical image diagnostic apparatus at the timing when the medical image diagnostic apparatus is turned on.

9. The medical image diagnostic apparatus according to claim 1, wherein
   the processing circuitry is configured to assign the function identified based on the grip portion to the medical image diagnostic apparatus at a timing before a start of examination.

10. The medical image diagnostic apparatus according to claim 1, wherein
    The processing circuitry is configured to assign the function identified based on the grip portion to the medical image diagnostic apparatus at the timing of receiving an instruction to update.

11. The medical image diagnostic apparatus according to claim 1, further comprising a memory that stores a position of the switch to which the grip portion is attached and the function assigned to the switch in association with each other,
    wherein, when the function associated with the grip portion is not recognized, the processing circuitry is configured to refer to the memory and to assign the same function as a previously assigned function to the switch to which the grip portion whose function is not recognized is attached.

12. The medical image diagnostic apparatus according to claim 1, further comprising a fixing portion to fix the grip portion.

13. The medical image diagnostic apparatus according to claim 1, wherein the switch comprises a foot switch that accepts foot operations.

14. The medical image diagnostic apparatus according to claim 2, wherein:
    the retention portion is provided on an accessory that is attached to the medical image diagnostic apparatus via an attachment portion; and
    the detection portion is provided on the attachment portion and detects the retention portion of the attached accessory.

15. The medical image diagnostic apparatus according to claim 1, further comprising a suppression portion provided on the grip portion and suppressing an operation other than an operation corresponding to a function associated with the grip portion.

16. A medical image diagnostic apparatus comprising:
a switch including a detachable grip portion; and
a suppression portion provided on the grip portion and suppressing an operation other than an operation corresponding to a function associated with the grip portion.

17. The medical image diagnostic apparatus according to claim 16, further comprising an input circuit to input a function to be assigned to the switch to which the grip portion is attached,
wherein the processing circuitry is configured to assign the functions input from the input circuit.

18. The medical image diagnostic apparatus according to claim 16, further comprising:
a display that displays a combination of the switch to which the grip portion is attached and functions that are able to be assigned to the switch; and
an input circuit to input a function to be assigned to the switch,
wherein the processing circuitry is configured to assign a function input from the input circuit.

19. An X-ray diagnostic apparatus that irradiates an object with an X-ray and detects the X-ray having passed through the object, the X-ray diagnostic apparatus comprising:
a switch including a detachable grip portion; and
processing circuitry configured to assign a function to the switch based on a type of the grip portion.

20. A console device for an X-ray diagnostic apparatus in which a plurality of switches to accept a corresponding plurality of operations on the X-ray diagnostic apparatus are provided, the console device comprising:
grip portions detachably attached to the switches; and
processing circuitry configured to assign a function to each of the plurality of switches based on a type of the attached grip portion.

* * * * *